United States Patent [19]

Szady et al.

[11] Patent Number: 6,018,076
[45] Date of Patent: Jan. 25, 2000

[54] ESTER PREPARATION

[75] Inventors: Michael J. Szady, Wayne; Ahmad Soltani-Ahmadi, Radnor, both of Pa.

[73] Assignee: Arco Chemical Technology, L.P., Greenville, Tex.

[21] Appl. No.: 09/030,171

[22] Filed: Feb. 25, 1998

Related U.S. Application Data

[63] Continuation-in-part of application No. 08/940,683, Sep. 30, 1997, Pat. No. 5,866,714.
[51] Int. Cl.[7] .................................................. C07C 67/04
[52] U.S. Cl. .............................................................. 560/247
[58] Field of Search ............................................. 560/247

[56] References Cited

U.S. PATENT DOCUMENTS

| | | |
|---|---|---|
| 3,031,495 | 4/1962 | Young et al. . |
| 3,096,365 | 7/1963 | Heisler et al. . |
| 3,678,099 | 7/1972 | Kemp . |
| 4,011,272 | 3/1977 | Matsuzawa et al. . |
| 4,593,135 | 6/1986 | Gregory .................................. 585/446 |
| 5,861,530 | 1/1999 | Atkins et al. ........................... 560/247 |

OTHER PUBLICATIONS

Pavlov, Bull. Soc. Chem. Fr., No. 12, pp. 2985–6, 1974.

*Primary Examiner*—Michael L. Shippen
*Attorney, Agent, or Firm*—William C. Long

[57] ABSTRACT

An olefin such as isobutylene is reacted with a carboxylic acid to produce the ester in the presence of an alkanol modifying agent effective to suppress olefin polymerization, at least part of the modifying agent being formed in situ by reaction of the olefin and water.

5 Claims, 1 Drawing Sheet

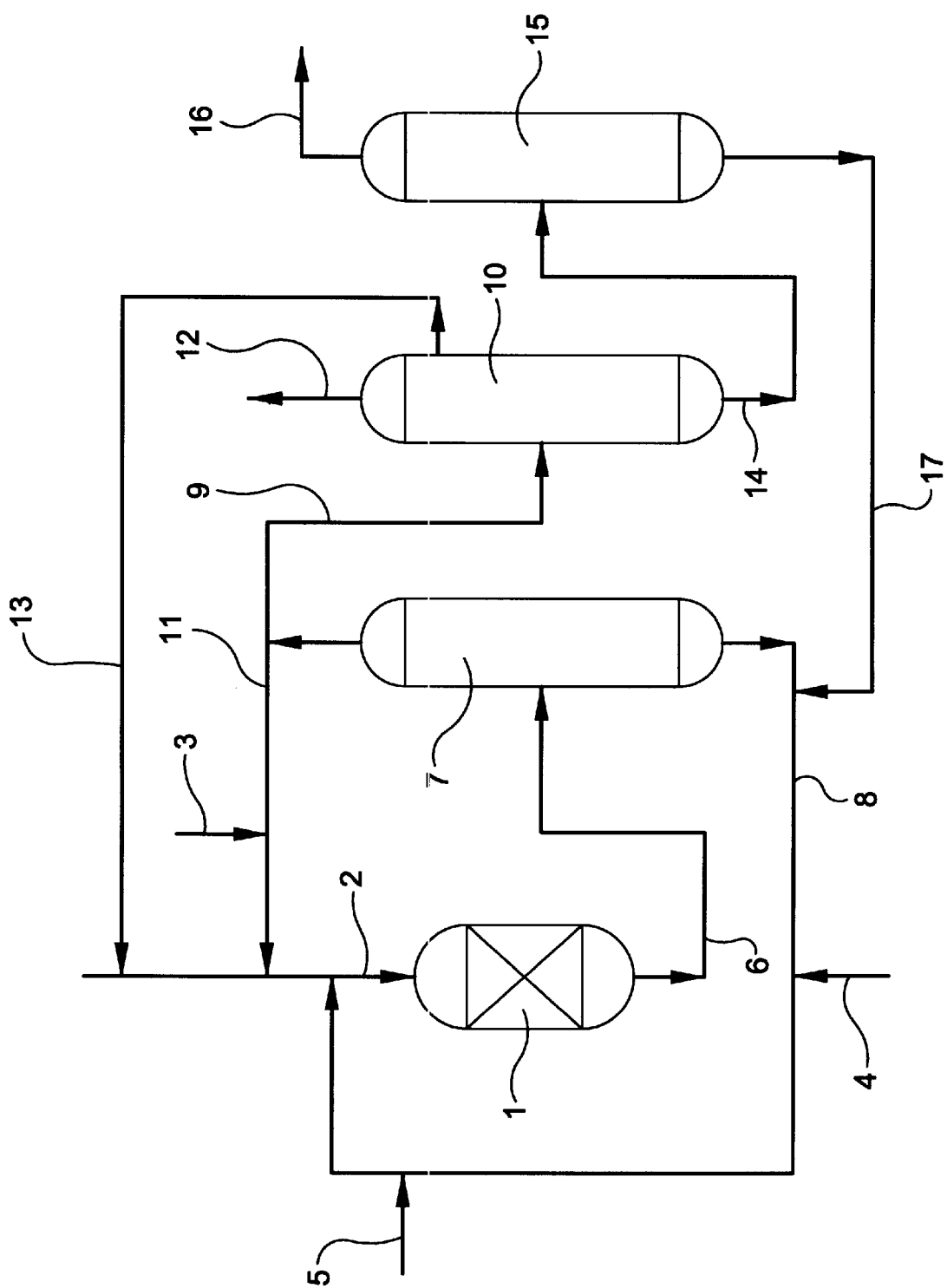

ESTER PREPARATION

RELATED APPLICATIONS

This application is a continuation-in-part of application Ser. No. 08/940,683 filed Sep. 30, 1997, now U.S. Pat. No. 5,866,714.

The present invention is related to the invention described in application Ser. No. 08/816,704; filed Mar. 13, 1997, now abandoned.

BACKGROUND OF THE INVENTION

1. Field of the Invention

The present invention provides an improved method for the preparation of esters such as t-butyl acetate.

2. Description of the Prior Art

It is known to produce esters by the reaction of an olefin such as isobutylene with a lower carboxylic acid over a sulfonate group-containing cation exchange resin. See U.S. Pat. No. 3,678,099 and the references disclosed therein including U.S. Pat. Nos. 2,678,332, 3,031,495, 3,172,905 and 3,173,943.

A problem which is encountered in such prior procedures has been the tendency for polymerization of the olefin to occur during the esterification which results both in significant yield losses and in the formation of products such as olefin dimer which are difficult to separate from the product ester. For example, isobutylene dimer forms an azeotrope with t-butyl acetate thus making separation exceedingly difficult.

In accordance with the invention of said copending application, the production of olefin oligomers during reaction between olefin and lower carboxylic acid is reduced by carrying out the reaction in the presence of a selectivity enhancing modifier such as t-butyl alcohol. However, the addition of the selectivity enhancing modifier to the reaction system involves an added expense and possibly results in purification problems where the modifier contains impurities.

U.S. Pat. No. 4,011,272 relates to a method for the production of tertiary butyl alcohol by reaction of isobutylene with water in the presence of a sulfonic acid resin and an organic acid such as acetic acid. Water is used in at least equimolar amount relative to the isobutylene and tertiary butyl alcohol is the primary product. The patent teaches that the minor amounts of tertiary butyl acetate which are formed can readily be hydrolyzed to form additional tertiary butyl alcohol.

BRIEF DESCRIPTION OF THE INVENTION

The present invention provides a process for the reaction of an olefin such as isobutylene with an acid such as acetic acid in the presence of a selectivity enhancing modifier such as t-butyl alcohol, the improvement being that the modifier is formed in situ by reaction of olefin and water which is introduced into the system. In addition, the invention provides for the removal of such olefin dimer as may be formed by azeotropic distillation with the selectivity enhancing modifier.

DESCRIPTION OF THE DRAWING

The attached drawing illustrates an embodiment of the invention.

DETAILED DESCRIPTION

The present invention, although applicable generally to the formation of esters having the formula

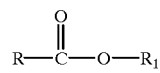

wherein $R_1$ is a $C_1$–$C_{10}$ alkyl group and R is hydrogen or a $C_1$–$C_{10}$ alkyl group, is especially applicable to the formation of esters wherein $R_1$ is a $C_4$ or $C_5$ tertiary alkyl group and R is hydrogen or a $C_1$–$C_2$ alkyl group. T-butyl acetate is an especially preferred product.

In carrying out the invention, olefin and organic carboxylic acid are reacted to form ester over a solid acidic catalyst in the presence of a modifying agent which enhances the selectivity for the ester formation reaction while suppressing the formation of olefin oligomers including olefin dimer. Especially preferred modifying agents are t-butyl alcohol. It is a special feature of the invention that the modifying agent is formed in situ by reaction of introduced water with olefin on contact with the solid acidic catalyst during the ester forming reaction.

The catalysts employed are known. See U.S. Pat. No. 3,678,099 the disclosure of which is incorporated herein by reference. Sulfonic acid-type exchange resins are especially useful as illustrated by Amberlyst A-15. Other known solid catalysts including acidic zeolites such as beta-zeolite, y-zeolite, and clays, and the like can be used.

The reaction is carried out in the liquid phase at relatively mild temperatures, eg. 10–100° C., preferably 15–50° C. and sufficient pressure to maintain the liquid phase. Reaction temperatures below about 40° C. are especially preferred.

The mol ratio of olefin to carboxylic acid can vary widely; excluding that amount of olefin needed to react with water to form the modifier, ratios of 0.05–10 mols olefin per mol carboxylic acid are generally useful, ratios of 0.1 to 0.5 mols olefin per mol carboxylic acid are especially useful. The higher amounts of acid relative to olefin improve reaction selectivity and further aid in suppressing dimer make.

The selectivity enhancing modifying agent should be present in an amount by weight of the total reaction mixture of at least about 2 wt %, preferably 4 to 40 wt % and most preferably 6–12 wt %.

The reaction is preferably carried out in a continuous fashion. Prior to or during start-up of the system, an inventory of the modifier is established either by charging an appropriate amount of the modifier to the system or by reaction of olefin and water within the system until the desired modifier concentration is established. Thereafter, water is added to the feed in amount sufficient to make up for the modifier which is lost to the system for example, by being removed with various process streams.

As an important feature, it is necessary that the feed to the solid acidic catalyst catalyzed esterification reaction contain no more than about 0.7 mols of water per mol of olefin, preferably no more than 0.6 mols of water per mol of olefin and most preferably no more than 0.1 mols of water per mol olefin. This is radically different from the process of U.S. Pat. No. 4,011,272 where water is used in amount of at least 1.0 mol of water per mol of olefin, and wherein the predominant reaction product is the alcohol and not the ester.

The accompanying drawing illustrates practice of the invention as it relates to the reaction of isobutylene with acetic acid in the presence of t-butanol selectivity enhancing modifier.

Referring to the drawing, reactor 1 is a fixed bed reactor packed with solid acidic catalyst, ie. Amberlyst A-15. A feed stream containing the net isobutylene and acetic acid reagents is continuously fed to reactor 1 via line 2. Net isobutylene is fed to the system via line 3 and net acetic acid is fed via line 4. Water is added to the system via line 5 preferably in amount equivalent to that needed to replenish the t-butanol which is used to azeotrope out diisobutylene impurity. It is preferred to form essentially all t-butanol in the system by reaction of water and isobutylene. However, less desirably some make up t-butanol from external sources can be added.

The feed composition introduced to reactor 1 via line 2 is controlled so as to provide both the desired mol ratio of acetic acid and isobutylene, ie 0.1–10 mols olefin per mol acetic acid and the appropriate amount of the t-butanol modifier, eg. at least 2% by weight of the reaction mixture.

The feed mixture is contacted in reactor 1 with the A-15 catalyst at conditions effective to form t-butyl acetate. At these same conditions, water in the feed reacts with isobutylene to form t-butanol thus to compensate for t-butanol losses from the system.

The reaction mixture comprised of unreacted isobutylene and acetic acid as well as t-butanol and t-butyl acetate product passes via line 6 from reactor 1 to distillation column 7 wherein a lighter components mixture comprised of isobutylene, t-butanol and t-butyl acetate is separated overhead from a bottom acetic acid stream which is recycled via line 8 to reactor 1.

A special advantage of this embodiment of the invention resides in the fact that the t-butanol modifier is useful for the removal of the small amount of diisobutylene by-product from the system. T-butanol forms a low boiling azeotrope with the diisobutylene and by providing a small pasteurization section at the top of column 10, virtually all the diisobutylene formed can be separated overhead via line 12 and discarded or otherwise worked up. Generally, the low boiling azeotrope contains about 2 to 25 wt % diisobutylene, t-butanol, and some ester which is about equal to the diisobutylene concentration; the azeotrope boils at about 76° C. at atmospheric pressure. Extractive distillation separation of the diisobutylene formed in the system is an effective and economically attractive method for producing high quality t-butyl acetate product.

T-butanol is removed from column 10 via line 13 and recycled to reactor 1. A bottoms stream from column 10 substantially free of diisobutylene and comprised of product t-butyl acetate together with some acetic acid passes via line 14 to column 15 wherein product t-butyl acetate is distilled overhead and recovered via line 16 with bottoms acetic acid removed via line 17 and recycled as indicated.

EXAMPLE

This example relates to practice of the invention wherein t-butyl acetate is formed by the reaction of isobutylene with acetic acid. The example is depicted in the FIGURE accompanying the present application.

Referring to the drawing, a feed mixture comprised of isobutylene and acetic acid is fed via line 2 to reactor 1. The reactor is packed with A-15 catalyst as described in the specification. The feed is introduced via line 2 at the rate of 479 lbs per hour and has the following composition: 13.0 wt % isobutylene, 73.9 wt % acetic acid, 7.9 wt % t-butyl alcohol, 4.7% tertiary butyl acetate and 0.5 wt % water. The reaction in reactor 1 is carried out at 27° C. and at a pressure of 75 psig. The weight hourly space velocity in reactor 1 is about 10 hr$^{-1}$.

In reactor 1, the water which forms part of the feed is reacted with isobutylene to form t-butanol, the selectivity enhancing modifier used in this practice of the invention. In addition, the reaction between isobutylene and acetic acid to form t-butyl acetate takes place.

The reaction mixture is removed from reactor 1 and passes at the rate of 479 lbs per hour via line 6 to distillation column 7. In column 7, the lower boiling components are distilled overhead at 98° C. and atmospheric pressure and the overhead mixture is resolved by partial condensation (not shown) into an isobutylene stream which is recycled at the rate of 28 lbs per hour via line 11 to reactor 1 and into a liquid stream comprised of t-butanol and t-butyl acetate which passes via line 9 at the rate of 154 lbs per hour to distillation line 10. The composition of this stream is about 25.7 wt % t-butanol, 58.3 wt % t-butyl acetate, 14.9 wt % acetic acid, 1.3 wt % water and 0.3 wt % diisobutylene by-product which is formed during the reaction in reactor 1.

Net make up isobutylene is introduced into the recycle line 11 via line 3 at the rate of 34 lbs per hour.

A bottoms stream from column 7 comprised of acetic acid is recycled via line 8 to the reactor 1. Added to this recycle stream is make up acetic acid which is introduced at the rate of 36 lbs per hour via line 4 and a recycle acetic acid stream from column 15 which is returned via line 17 to line 8.

The small amount of water needed to balance t-butanol losses in the system is introduced at the rate of 1 lbs per hour via line 5.

In column 10, a small pasteurization section is provided at the top and a low boiling t-butanol and diisobutylene azeotrope is removed overhead at 76° C. and atmospheric pressure via line 12. The stream is removed at the rate of 4 lbs per hour and comprises 12.5 wt % diisobutylene, 12.5 wt % tertiary butyl acetate, 12.5 wt % water, and 62.5 wt % t-butanol.

A t-butanol stream is removed from the upper portion of column 10 and is recycled at the rate of 53 lbs per hour via line 13 to reactor 1.

A bottoms stream from column 10 comprised of tertiary butyl acetate product together with acetic acid is removed at 103° C. and atmospheric pressure via line 14 and passes at the rate of 97 lbs per hour to distillation column 15. This stream has the composition 76.3 wt % tertiary butyl acetate and 23.7 wt % acetic acid.

In column 15, product t-butyl acetate is removed overhead at the rate of 67 lbs per hour at 97° C. and atmospheric pressure. This product stream has a t-butyl acetate purity of ≧99.5%.

A bottoms acetic acid stream is removed from column 15 at the rate of 30 lbs per hour at 111° C. and atmospheric pressure and is recycled as above described via line 17 to line 8 and ultimately back to reactor 1.

As can be seen from the results presented, practice of the present invention provides an efficient and effective procedure for the preparation of esters through the reaction of an olefin such as isobutylene with an acid such as acetic acid. The provision of the selectivity enhancing modifier ensures a high selectivity for the reaction system. The formation of the modifier by the in situ reaction of water and the olefin ensures that the formed alcohol is of high quality and absent the types of impurities which are normally associated with such alcohols and also provides an extremely inexpensive method for providing the necessary inventory of the modifier alcohol.

We claim:

1. In a continuous process for the reaction of isobutylene with acetic acid in the liquid phase at a temperature in the range 10–100° C. in the presence of a solid acidic catalyst to selectively form t-butyl acetate wherein t-butanol selectivity enhancing modifier is present during the reaction in amount sufficient to enhance selectivity of the reaction to t-butyl acetate and to suppress isobutylene polymerization, the improvement which comprises continuously forming at least part of the t-butanol modifier during said reaction by reaction of isobutylene and water which are continuously fed to the reaction.

2. The process of claim 1 wherein the amount of water continuously fed to the reaction is no more than about 0.7 mols of water per mol of isobutylene.

3. The process of claim 1 wherein the amount of water continuously fed to the reaction is no more than about 0.6 mols of water per mol of isobutylene.

4. The process of claim 1 wherein the amount of water continuously fed to the reaction is no more than 0.1 mols of water per mol of isobutylene.

5. The process of claim 1 wherein the solid acidic catalyst is a sulfonic acid resin catalyst.

* * * * *